United States Patent
Merkel et al.

(10) Patent No.: US 9,994,502 B1
(45) Date of Patent: Jun. 12, 2018

(54) PROCESS FOR THE PRODUCTION OF 1-CHLORO-3,3,3-TRIFLUOROPROPENE (HCFO-1233ZD)

(71) Applicant: Honeywell International Inc., Morris Plains, NJ (US)

(72) Inventors: Daniel C. Merkel, Orchard Park, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days. days.

(21) Appl. No.: 15/883,581

(22) Filed: Jan. 30, 2018

(51) Int. Cl.
C07C 17/25 (2006.01)
C07C 17/20 (2006.01)
C07C 17/383 (2006.01)

(52) U.S. Cl.
CPC ............ *C07C 17/206* (2013.01); *C07C 17/25* (2013.01); *C07C 17/383* (2013.01)

(58) Field of Classification Search
CPC .............................. C07C 17/25; C07C 17/206
See application file for complete search history.

(56) References Cited

U.S. PATENT DOCUMENTS

| | | | |
|---|---|---|---|
| 6,166,274 A | 12/2000 | Chen et al. | |
| 6,844,475 B1 | 1/2005 | Tung et al. | |
| 7,829,747 B2 | 11/2010 | Wang et al. | |
| 8,202,617 B2 | 6/2012 | Kitahara et al. | |
| 8,217,208 B2 | 7/2012 | Hulse et al. | |
| 8,618,338 B2 | 12/2013 | Elsheikh et al. | |
| 8,704,017 B2 | 4/2014 | Pokrovski et al. | |
| 8,779,218 B2 | 7/2014 | Pigamo et al. | |
| 8,835,700 B2 | 9/2014 | Pokrovski et al. | |
| 8,921,621 B2 | 12/2014 | Cottrell et al. | |
| 9,018,430 B2 | 4/2015 | Merkel et al. | |
| 9,024,092 B2 | 5/2015 | Merkel et al. | |
| 9,045,386 B2 | 6/2015 | Tung et al. | |
| 9,102,579 B2 | 8/2015 | Light et al. | |
| 9,102,580 B2 | 8/2015 | Nappa et al. | |
| 9,328,043 B2 | 5/2016 | Wang et al. | |
| 9,334,206 B2 | 5/2016 | Wang et al. | |
| 2016/0332936 A1 | 11/2016 | Wang et al. | |

FOREIGN PATENT DOCUMENTS

JP 2017124997 A 7/2017
WO 2016009946 A1 1/2016

OTHER PUBLICATIONS

WO2016009946 (A1), Jan. 21, 2016, pp. 1-15; English translation (Year: 2016).*

* cited by examiner

*Primary Examiner* — Medhanit W Bahta
(74) *Attorney, Agent, or Firm* — Faegre Baker Daniels LLP

(57) ABSTRACT

A process for enhancing the selective and efficient production of (E)-1-chloro-3,3,3-trifluoropropene (HCFO-1233zd (E), or 1233zd(E)). During the manufacture of HCFO-1233zd(E) by fluorination of 1,1,1,3,3-pentachloropropane (HCC-240fa), a by-product of 1,3,3-trichloro-1,1-difluoropropane (HCFC-242fa) is separated and then dehydrochlorinated to form 1,3-chloro-3,3-difluoropropene (HCFO-1232zd). The HCFO-1232zd is then fluorinated to form HCFO-1233zd(E).

19 Claims, 9 Drawing Sheets

Fig. 7

Comparison of HCC-240fa, HCFC-242fa, and HCFO-1232zd feedstocks to make HCFO-1233zd
(140°C and 1 hour hold time)

| Exp# | Temp (oC) | HF charged (g) | HF charged (mol) | 240fa charged (g) | 240fa charged (mol) | HF:240fa mole ratio | Hold time (hr) | 240fa conv (%) |
|---|---|---|---|---|---|---|---|---|
| 1 | 140 | 84.4 | 4.2 | 53.4 | 0.2 | 17.1 | 1.0 | 99.5 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 0.41 | 0 | 5.29 | 0.06 | 66.30 | 1.91 | 3.96 | 0.97 | 1.14 | 19.10 | 0.86 |

| Exp# | Temp (oC) | HF charged (g) | HF charged (mol) | 242fa charged (g) | 242fa charged (mol) | HF:242fa mole ratio | Hold time (hr) | 242fa conv (%) |
|---|---|---|---|---|---|---|---|---|
| 2 | 140.0 | 95.8 | 4.8 | 51.0 | 0.3 | 17.2 | 1.0 | 4.4 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 9.58 | 0.08 | 18.86 | 0.19 | 32.37 | 0.55 | 2.37 | 18.19 | 0.50 | 7.18 | 10.13 |

| Exp# | Temp (oC) | HF charged (g) | HF charged (mol) | 1232zd charged (g) | 1232zd charged (mol) | HF:1232zd mole ratio | Hold time (hr) | 1232zd conv (%) |
|---|---|---|---|---|---|---|---|---|
| 3 | 140 | 96.9 | 4.8 | 40.9 | 0.28 | 17.4 | 1.0 | 99.8 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 0.01 | 0.27 | 0.55 | 0.05 | 89.46 | 3.61 | 1.69 | 4.21 | 0.13 | 0.01 | 0.26 |

Fig. 8

Comparison of HCC-240fa, HCFC-242fa, and HCFO-1232zd feedstocks to make HCFO-1233zd
(130°C and 3 hour hold time)

| Exp# | Temp (oC) | HF charged (g) | HF charged (mol) | 240fa charged (g) | 240fa charged (mol) | HF:240fa mole ratio | Hold time (hr) | 240fa conv (%) |
|---|---|---|---|---|---|---|---|---|
| 4 | 130 | 85.2 | 4.3 | 53.2 | 0.2 | 17.3 | 3.0 | 99.5 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 0.02 | 0 | 3.23 | 0.06 | 77.01 | 0.40 | 4.73 | 0.83 | 2.78 | 10.15 | 0.46 |

| Exp# | Temp (oC) | HF charged (g) | HF charged (mol) | 242fa charged (g) | 242fa charged (mol) | HF:242fa mole ratio | Hold time (hr) | 242fa conv (%) |
|---|---|---|---|---|---|---|---|---|
| 5 | 130.0 | 94.3 | 4.7 | 50.1 | 0.3 | 17.3 | 3.0 | 3.9 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 9.80 | 0.17 | 11.34 | 0.50 | 28.31 | 0.56 | 4.15 | 26.44 | 0.46 | 4.26 | 14.00 |

| Exp# | Temp (oC) | HF charged (g) | HF charged (mol) | 1232zd charged (g) | 1232zd charged (mol) | HF:1232zd mole ratio | Hold time (hr) | 1232zd conv (%) |
|---|---|---|---|---|---|---|---|---|
| 6 | 130.0 | 90.1 | 4.5 | 41.8 | 0.3 | 15.8 | 3.0 | 99.9 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 0.04 | 0.24 | 0.42 | 0.10 | 94.30 | 0.41 | 1.67 | 2.75 | 0.07 | 0.00 | 0.67 |

Fig. 9

Comparison of HCFC-242fa and HCFO-1232zd feedstocks to make HCFO-1233zd
(130°C and 1 hour hold time)

| Exp# | Temp (oC) | HF charged (g) | 242fa charged (g) | 242fa charged (mol) | HF:242fa mole ratio | Hold time (hr) | 242fa conv (%) |
|---|---|---|---|---|---|---|---|
| 7 | 130.0 | 94.3 | 50.1 | 0.3 | 17.3 | 1.0 | 1.6 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 10.62 | 0.30 | 3.81 | 0.81 | 18.24 | 0.58 | 2.20 | 36.79 | 0.63 | 8.15 | 17.87 |

| Exp# | Temp (oC) | HF charged (g) | 1232zd charged (g) | 1232zd charged (mol) | HF:1232zd mole ratio | Hold time (hr) | 1232zd conv (%) |
|---|---|---|---|---|---|---|---|
| 8 | 130 | 88.1 | 50.1 | 0.34 | 12.9 | 1.0 | 100.0 |

By-Product Selectivities (mol%)

| TFPy | 1234ze(E) | 245fa | 1234ze(Z) | 1233zd(E) | 244fa | 1233zd(Z) | 243 iso's | 242 iso's | 241 iso | others |
|---|---|---|---|---|---|---|---|---|---|---|
| 0.00 | 0.09 | 0.09 | 0.02 | 93.56 | 0.13 | 2.07 | 4.10 | 0.07 | 0.00 | 0.37 |

PROCESS FOR THE PRODUCTION OF 1-CHLORO-3,3,3-TRIFLUOROPROPENE (HCFO-1233ZD)

BACKGROUND

1. Field of the Disclosure

The present disclosure relates to a process for enhancing the selective and efficient production of 1-chloro-3,3,3-trifluoropropene (HCFO-1233zd, or 1233zd) and, in particular, to a process for enhancing the selective and efficient production of HCFO-1233zd(E).

2. Description of the Related Art

Fluorocarbon based fluids have found widespread use in industry in a number of applications, including use as refrigerants, aerosol propellants, blowing agents, heat transfer media, and gaseous dielectrics. Due to suspected environmental problems associated with the use of some of these fluids, including the relatively high global warming potentials associated therewith, it is desirable to use fluids having the lowest possible global warming potential (GWP) in addition to also having zero ozone depletion potential (ODP). Thus, there is considerable interest in developing environmentally friendlier materials for various applications, such as those mentioned above.

Hydrochlorofluoroolefins (HCFOs) having zero ozone depletion and low global warming potential have been identified as potentially filling this need. However, the toxicity, boiling point, and other physical properties of such chemicals vary greatly from isomer to isomer. One HCFO having valuable properties is (E)-1-chloro-3,3,3-trifluoropropene (HCFO-1233zd(E)), which has been proposed as a next generation non ozone depleting and low global warming potential solvent.

(E)-1-chloro-3,3,3-trifluoropropene (HCFO-1233zd(E), or 1233zd(E)) is a new Low Global Warming and Non-Ozone Depleting molecule, which has applications as a blowing agent, solvent, and refrigerant. The applications and interest in this molecule have resulted in the development of several manufacturing processes for its production.

In one commercial process, HCFO-1233zd(E) is produced by fluorination of 1,1,1,3,3-pentachloropropane (HCC-240fa) using hydrofluoric acid (HF). However, in this process, various by-products are formed, such as 1,3,3-trichloro-1,1-difluoropropane (HCFC-242fa), which compromise the selectivity and efficiency of the production of HCFO-1233zd(E).

What is needed is an improved method for the production of HCFO-1233zd(E).

SUMMARY

The present disclosure relates to a process for enhancing the selective and efficient production of (E)-1-chloro-3,3,3-trifluoropropene (HCFO-1233zd(E), or 1233zd(E)). During the manufacture of HCFO-1233zd(E) by fluorination of 1,1,1,3,3-pentachloropropane (HCC-240fa), a by-product of 1,3,3-trichloro-1,1-difluoropropane (HCFC-242fa) is separated and then dehydrochlorinated to form 1,3-dichloro-3,3-difluoropropene (HCFO-1232zd). The HCFO-1232zd is then fluorinated to form HCFO-1233zd(E).

In one form thereof, the present disclosure provides a process for the production of 1-chloro-3,3,3-trifluoropropene (HCFO-1233zd), including the steps of: providing a reactant composition including 1,3,3-trichloro-1,1-difluoropropane (HCFC-242fa); dehydrochlorinating the HCFC-242fa in the presence of a basic solution to form 1,3-dichloro-3,3-difluoropropene (HCFO-1232zd); and fluorinating the HCFO-1232zd with hydrogen fluoride (HF) to produce HCFO-1233zd.

Following the fluorinating step, the HCFO-1233zd produced may be predominantly HCFO-1233zd(E).

The dehydrochlorinating step may be performed at a temperature between 0° C. and 100° C. The fluorinating step may be performed at a temperature between 80° C. and 150° C. The fluorinating step may be performed in the absence of a catalyst.

The reactant composition may further include hydrogen fluoride (HF) and the process may further include the additional step, after the providing step and prior to the dehydrochlorinating step, of separating HF from the reactant composition.

The process may further include the additional step, after the dehydrochlorinating step and prior to the fluorinating step, of drying the HCFO-1232zd.

The basic solution in the dehydrochlorinating step may be selected from the group consisting of potassium hydroxide (KOH), sodium hydroxide (NaOH), and calcium hydroxide (CaOH).

In another form thereof, the present disclosure provides a process for the production of 1-chloro-3,3,3-trifluoropropene (HCFO-1233zd), including the steps of: fluorinating 1,1,1,3,3-pentachloropropane (HCC-240fa) with hydrofluoric acid (HF) to produce a product stream including HCFO-1233zd and 1,3,3-trichloro-1,1-difluoropropane (HCFC-242fa); separating HCFC-242fa from the product stream; dehydrochlorinating the HCFC-242fa in a liquid phase in the presence of a basic solution to form 1,3-dichloro-3,3-difluoropropene (HCFO-1232zd); and fluorinating the HCFO-1232zd with hydrogen fluoride (HF) to produce HCFO-1233zd.

The first fluorinating step may be performed at a reaction temperature between 120° C. and 140° C. and at a reaction pressure of between 230 psig and 400 psig.

Following the second fluorinating step, the HCFO-1233zd produced may be predominantly HCFO-1233zd(E). The dehydrochlorinating step may be performed at a temperature between 0° C. and 100° C.

The second fluorinating step may be performed at a temperature between 80° C. and 150° C. The second fluorinating step may be performed in the absence of a catalyst.

The reactant composition may further include hydrogen fluoride (HF) and the process may further include the additional step, after the first fluorinating step and prior to the dehydrochlorinating step, of separating HF from the product stream.

The process may further include the additional step, after the dehydrochlorinating step and prior to the second fluorinating step, of drying the HCFO-1232zd.

The process may further include the additional step, after the second fluorinating step, of recycling at least one of unreacted HCFO-1232zd and unreacted HF back to the first fluorinating step.

The separating step may be conducted via vacuum distillation. The separating step may be conducted via distillation at a pressure between 10 torr and 5,200 torr.

The above mentioned and other features of the disclosure, and the manner of attaining them, will become more apparent and the disclosure itself will be better understood by reference to the following description of embodiments of the disclosure taken in conjunction with the accompanying drawings.

BRIEF DESCRIPTION OF THE DRAWINGS

The above mentioned and other features of the disclosure, and the manner of attaining them, will become more apparent and the disclosure itself will be better understood by reference to the following description of embodiments of the disclosure taken in conjunction with the accompanying drawings.

FIG. 7 corresponds to Example 5, and is a table showing a comparison of HCC-240fa, HCFC-242fa, and HCFO-1232zd feedstocks to make HCFO-1233zd (140° C. and 1 hour hold time);

FIG. 8 corresponds to Example 5, and is a table showing a comparison of HCC-240fa, HCFC-242fa, and HCFO-1232zd feedstocks to make HCFO-1233zd (130° C. and 3 hour hold time); and FIG. 9 corresponds to Example 5, and is a table showing a comparison of HCFC-242fa, and HCFO-1232zd feedstocks to make HCFO-1233zd (130° C. and 1 hour hold time).

Figure 1:
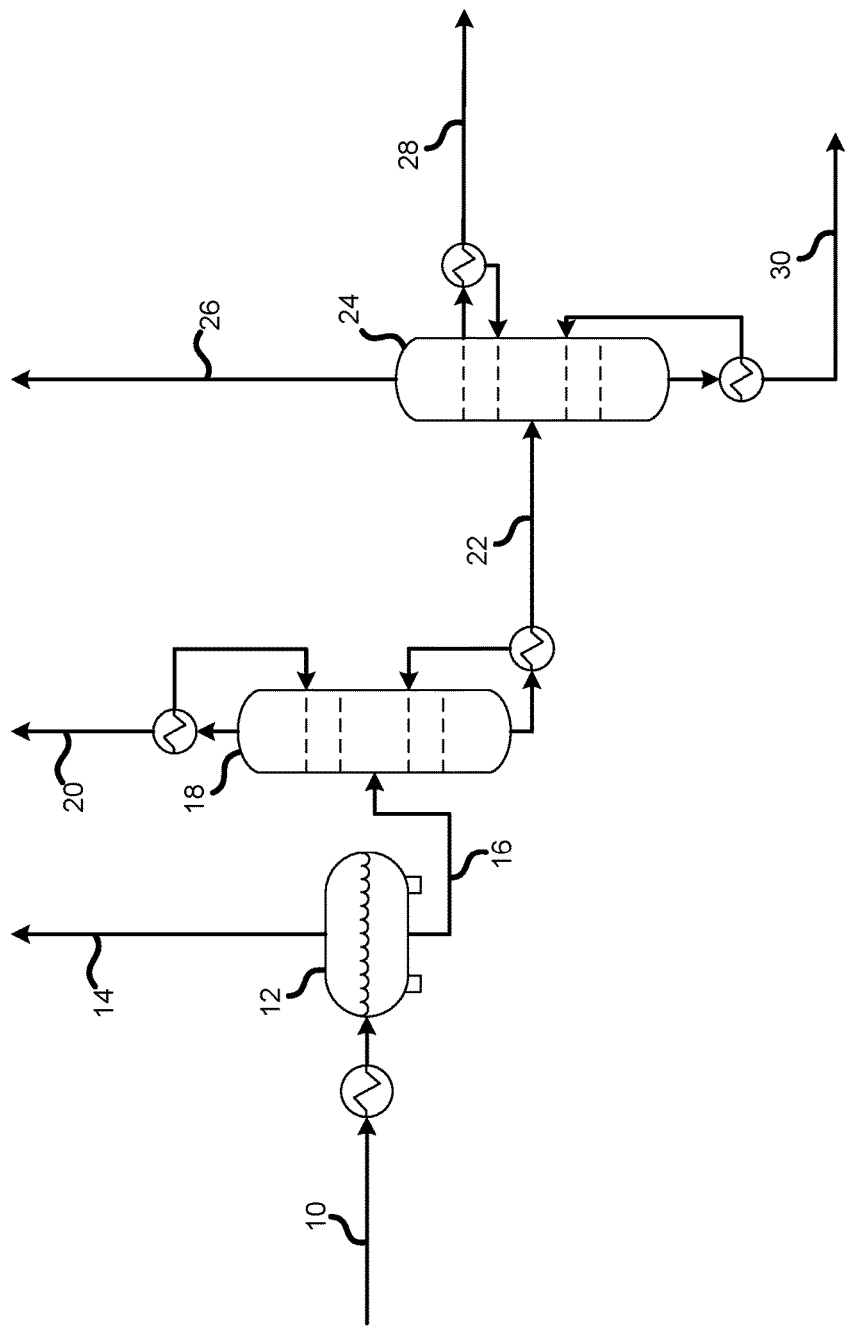
FIG. 1 is a schematic diagram of the first step of the present process according to a first embodiment.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates an embodiment of the disclosure, and such exemplification is not to be construed as limiting the scope of the disclosure in any manner.

DETAILED DESCRIPTION

The present disclosure relates to a process for enhancing the selective and efficient production of (E)-1-chloro-3,3,3-trifluoropropene (HCFO-1233zd(E), or 1233zd(E)). During the manufacture of HCFO-1233zd(E) by fluorination of 1,1,1,3,3-pentachloropropane (HCC-240fa), a by-product of 1,3,3-trichloro-1,1-difluoropropane (HCFC-242fa) is separated and then dehydrochlorinated to form 1,3-dichloro-3,3-difluoropropene (HCFO-1232zd). The HCFO-1232zd is then fluorinated to form HCFO-1233zd(E).

I. Background

The overall chemical equation for the non-catalytic reaction of HCC-240fa and hydrogen fluoride (HF) to form 1-chloro-3,3,3-trifluoropropene (HCFO-1233zd) is set forth below as Equation (I):

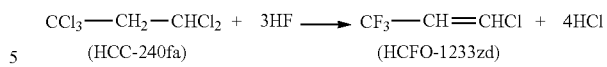

$$CCl_3-CH_2-CHCl_2 + 3HF \longrightarrow CF_3-CH=CHCl + 4HCl$$
(HCC-240fa) (HCFO-1233zd)

Typically, the foregoing reaction is performed without a catalyst in an agitated liquid phase reactor at a reaction temperature of 120-140° C. and a reaction pressure of 230-400 psig.

It is believed that the foregoing overall reaction has two distinct reaction pathways, including a desired pathway, set forth below in Equation (II), and a competing pathway, set forth below in Equation (III):

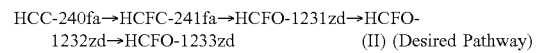

HCC-240fa→HCFC-241fa→HCFO-1231zd→HCFO-1232zd→HCFO-1233zd  (II) (Desired Pathway)

HCC-240fa→HCFC-241fa→HCFC-242fa→HCC-243 isomers  (III) (Competing pathway)

In the desired pathway of Equation (II), HCC-240fa is converted to 1,1,3,3-tetrachloro-1-fluoropropane (HCFC-241fa), which is then converted to 1,3,3-A trichloro-3-fluoropropene (HCFO-1231zd), which is then converted to 1,3-dichloro-3,3-difluoropropene (HCFO-1232zd), which is then converted to HCFO-1233zd.

However, in the competing pathway of Equation (III), HCC-240fa is converted to HCFC-241fa, and then to 1,3,3,-trichloro-1,1-difluoropropane (HCFC-242fa), which disadvantageously will not react further to form HCFO-1233zd but rather will react to form various isomers of 1,2-dichloro-3,3,3-trifluoropropane (HCFC-243).

It has been found that the desired pathway of Equation (II), which includes the saturated intermediate HCFC-241fa, has an overall relatively low selectivity of only about 65% to HCFO-1233zd. It is believed that the low selectivity can mostly be attributed to the formation of the saturated by-product HCFC-242fa via the non-catalytic reaction of HCFC-241fa with anhydrous HF under the foregoing reaction conditions according to the competing pathway of Equation (III).

It has also been established experimentally by the present inventors that HCFC-242fa conversion to HCFO-1233zd in the presence of anhydrous HF under the foregoing non-catalytic reaction conditions is very low (<4.5%), such that HCFC-242fa is essentially unreactive in producing HCFO-1233zd under the foregoing non-catalytic reaction conditions. Therefore, HCFC-242fa is not recyclable in the non-catalytic HCFO-1233zd process.

This can be seen in a gas chromatography (GC) analysis of the HCFO-1233zd crude product that is produced by the foregoing non-catalytic process, wherein analysis shows that the major component of all of the high boiling by-products of HCFO-1233zd which are produced in the process is HCFC-242fa.

In Table I below, an exemplary average composition is set forth of a HCFO-1233zd crude product stream from a continuous non-catalytic process performed under the foregoing reaction conditions downstream of a recycle column which returns a bottoms stream containing the majority of the unreacted anhydrous HF and HCC-240fa, and intermediates HCFO-1231zd, HCFO-1232zd, and HCFC-241fa back to the reactor for further conversion, as discussed below.

In Table I below, high boiling by-products are set forth in boldface.

TABLE I

| Component | Wt. % |
|---|---|
| HF | 1.9 |
| HFC-245fa | 0.14 |
| HFO-1234ze isomer 1 | 0.69 |
| HFO-1234ze isomer 2 | 0.20 |
| HCFC-244fa | 0.74 |
| HCFO-1233zd isomers | 79.46 |
| HCFC-243 isomers | 2.06 |
| HCFC-242fa | 13.44 |
| HCFC-242fb | 0.32 |
| HCFC-241 isomer | 0.73 |
| HCFO-1232 isomers | 0.04 |
| Others | 0.29 |

In the above process, HCFC-242fa must be separated from the HCFO-1233zd crude stream along with the other high boiling impurities set forth in Table I above. The high boiling impurities, including as a majority component HCFC-242fa, are then undesirably disposed of as hazardous waste at a high cost and therefore account for a significant yield loss in the HCFO-1233zd non-catalytic manufacturing process.

II. Overview of the Present Process

In view of the concerns discussed above, it is desirable to improve the overall yield of the non-catalytic HFCO-1233zd process by utilizing the HCFC-242fa by-product and shortening the overall residence time of the HCFO-1233zd reaction. The slowest reaction rate, or rate determining step, is the reaction of HFCF-241fa to HCFO-1231zd in Equation (II) above, though unfortunately there is the competing reaction of HCFC-241fa to HCFC-242fa per Equation (III) above, and the slow reaction rate of Equation (II) provides ample time for the competing reaction to occur such that the overall selectivity to HCFO-1233zd is only about 75 to 85%.

According to the present process, HCFC-242fa produced in the HCC-240fa reaction of Equation (III) is first separated or isolated from the HCFO-1233zd crude stream, and is then dehydrochlorinated in the presence of a basic solution, such as potassium hydroxide (KOH), to form HCFO-1232zd according to Equation (IV) below:

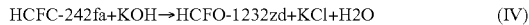
HCFC-242fa+KOH→HCFO-1232zd+KCl+H2O    (IV)

Then, the HCFO-1232zd formed may be introduced into a non-catalytic reactor, either by itself, or optionally, in combination with HCC-240fa. Advantageously, the HCFO-1232zd will react very quickly via a fluorination reaction with hydrogen fluoride to form the desired end product HCFO-1233zd with high selectivity according to Equation (V) below:

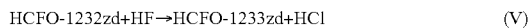
HCFO-1232zd+HF→HCFO-1233zd+HCl    (V)

The present inventors have observed that, based on the fact that the fastest path to make HCFO-1233zd from HCC-240fa is to proceed through progressive reaction via the unsaturates wherein HCFO-1231zd is reacted to form HCFO-1232zd which is thence reacted to form HCFO-1233zd according to Equation (II) above, as well as to avoid the yield loss and disposal costs from producing HCFC-242fa from HFC-F241fa, the present process is effective to increase the yield of the main HCFO-1233zd process by first converting the HCFC-242fa with high yield to a unsaturated hydrochlorofluoro-olefin (HCFO), namely HCFO-1232zd, by dehydrochlorination, which in turn reacts readily with hydrogen fluoride without a catalyst to form HCFO-1233zd in good yield. In this manner, the present process improves the overall yield of the HFCO-1233zd non-catalytic process by converting a major by-product into an intermediate that reacts readily to the desired HCFO-1233zd product.

In the first step of the present process, a HCFC-242fa crude by-product stream is separated, or isolated, from the main reaction by which HCC-240fa is reacted with hydrogen fluoride (HF) to form HCFO-1233zd. This can be readily accomplished by using batch or continuous distillation to remove the high boiling by-products from the HCFO-1233zd crude stream. Relatively pure HCFC-242fa may then be isolated using additional batch or continuous distillation under vacuum or at pressure.

Vacuum distillation may improve the separation by one or more of the following attributes: (1) prevention of product degradation because of reduced pressure leading to lower distillation column bottoms temperatures, (2) reduction of product degradation because of reduced mean residence time, especially in columns using packing rather than trays, and (3) increasing capacity, yield, and purity. Another advantage of vacuum distillation is the reduced capital cost, at the expense of slightly more operating cost. Utilizing vacuum distillation may reduce the height and diameter, and thus the capital cost, of a distillation column.

Typically, this distillation may be run at pressures as little as 10 torr, 100 torr, or 500 torr, or as great as 1,000 torr, 2,500 torr, or 5,200 torr, or within any range defined between any pair of the foregoing values, such as 10 to 5,200 torr, 100 to 2,500 torr, or 500 to 1,000 torr, for example.

The second step of the present process is the conversion of HCFC-242fa to HCFO-1232zd by dehydrochlorination using a basic solution, such as a 1-50 wt. % basic solution, for example, according to Equation (IV) above. Of note, this step may be considered the first step of the present process if HCFC-242fa is obtained from an alternative source.

The basic solution may include one or more of potassium hydroxide (KOH), sodium hydroxide (NaOH), calcium hydroxide (CaOH), or any other alkali earth metal or alkali metal hydroxide. The foregoing reaction may be performed in an agitated liquid phase reactor at a reaction pressure of 500 to 3300 torr. The reaction may be run at relatively low temperatures as little as 0° C., 25° C., or 40° C., or at temperatures as high as 60° C., 75° C., or 100° C., or within any range defined between any two of the foregoing values, such as 0° C. to 100° C., 25° C. to 75° C., or 40° C. to 60° C., for example. The selectivity to HCFO-1232zd in an experimental reaction was >90.7%.

The HCFO-1232zd crude stream may then be dried using a desiccant such as molecular sieves, calcium sulfate, magnesium sulfate, sulfuric acid, or silica gel, for example, and may then be conveyed to the third step of the present process.

Optionally, relatively pure HCFO-1232zd may then be isolated using continuous or batch distillation under vacuum or at pressure. This distillation may be run at pressures as little as 10 torr, 100 torr, or 500 torr, or as great as 1,000 torr, 2,500 torr, or 5,200 torr, or within any range defined between any pair of the foregoing values, such as 10 to 5,200 torr, 100 to 2,500 torr, or 500 to 1,000 torr, for example.

In the third step of the present process, the dried HCFO-1232zd, or dried and purified HCFO-1232zd, is fed to a fluorination reactor where the HCFO-1232zd stream is fluorinated to form the desired HCFO-1233zd product according to Equation (V) above. The reactor may be an agitated liquid phase fluorination reactor, for example. Further, the reactor may be the same reactor used for the fluorination of HCFC-240fa, or the reactor may be a dedicated, stand-alone reactor used only for the fluorination of the HCFO-1232zd crude stream to form the desired HCFO-1233zd product. The fluorination reaction may run at temperatures as little as 50° C., 80° C., or 100° C., or as high as 125° C., 150° C., or 200° C., or within any range defined between any two of the foregoing values, such as 50° C. to 200° C., 80° C. to 150° C., or 100° C. to 125° C., for example. The fluorination reaction may be performed at a reaction pressure as little as 100 psig or 200 psig or as great as 350 psig or 500 psig, or within any range defined between any two of the foregoing values, such as 100 to 500 psig or 200 to 350 psig, for example. Suitable HF to HCFO-1231zd ratios for the fluorination reaction may be as little as 2:1, 5:1, or 10:1, or as great as 50:1, 75:1, or 100:1, or within any range defined between any two of the foregoing values, such as 2:1 to 100:1, 5:1 to 75:1, or 10:1 to 50:1, for example. It has been found that fluorination of HCFO-1232zd with anhydrous HF at 80-150° C. produces HCFO-1233zd(E) with a relatively high conversion of greater than 95% and a relatively high selectivity of greater than 90%. Unreacted anhydrous HF and unreacted HCFO-1232zd, and/or any other by-products which may be formed, may be recycled back to the reactor for further processing.

The HCFO-1233zd crude product may be purified by conventional techniques such as distillation or scrubbing/drying to remove the HCl co-product, phase separation and/or scrubbing/drying to remove any residual HF and/or moisture, and distillation to remove any organic impurities. The HCFO-1233zd may be predominantly HCFO-1233zd(E), meaning that the amount of HCFO-1233zd(E) is greater than the amount of any HCFO-1233zd(Z) which may be present in the purified composition.

Various embodiments of the present process are described in further detail below with reference to FIGS. 1-6.

III. Schematics of the Present Process

Referring to FIGS. 1-6, schematics of the present process are presented, showing the first, second, and third steps of the present process which may be performed under the general process conditions set forth above.

Referring to FIG. 1, a schematic of the first step of the present process is shown according to a first embodiment. A product stream from the non-catalytic fluorination of HCC-240fa with hydrogen fluoride (HF) to form HCFO-1233zd, which product stream includes HF and HCFO-1233zd, is conveyed from a fluorination reactor, recycle distillation column, and HCl recovery distillation column (not shown) via line 10 to phase separator 12. In phase separator 12, HF and HCFO-1233zd separate via gravity, and the upper phase HF is recycled back to the fluorination reactor (not shown) via recycle line 14. The lower phase HCFO-1233zd is removed from phase separator 12 via line 16 and then passes to distillation column 18. Crude HCFO-1233zd is removed from distillation column 18 in overhead stream 20 and is then sent to a washing, drying, and purification stage not described in further detail herein. Crude HCFC-242fa is removed from column 18 in bottoms stream 22 and passes to a batch distillation column 24. Low boiling by-products are removed from column 24 in overhead stream 26 and are sent to collection or waste disposal. Higher purity HCC-240fa is removed from column 24 via line 28 to the second step of the present process, as described below. High boiling by-products in bottom stream 30, such as HCFC-241fa, 1233zd dimers, and other halogenated compounds containing 4 or more carbon atoms, are sent to collection or waste disposal.

Figure 2:
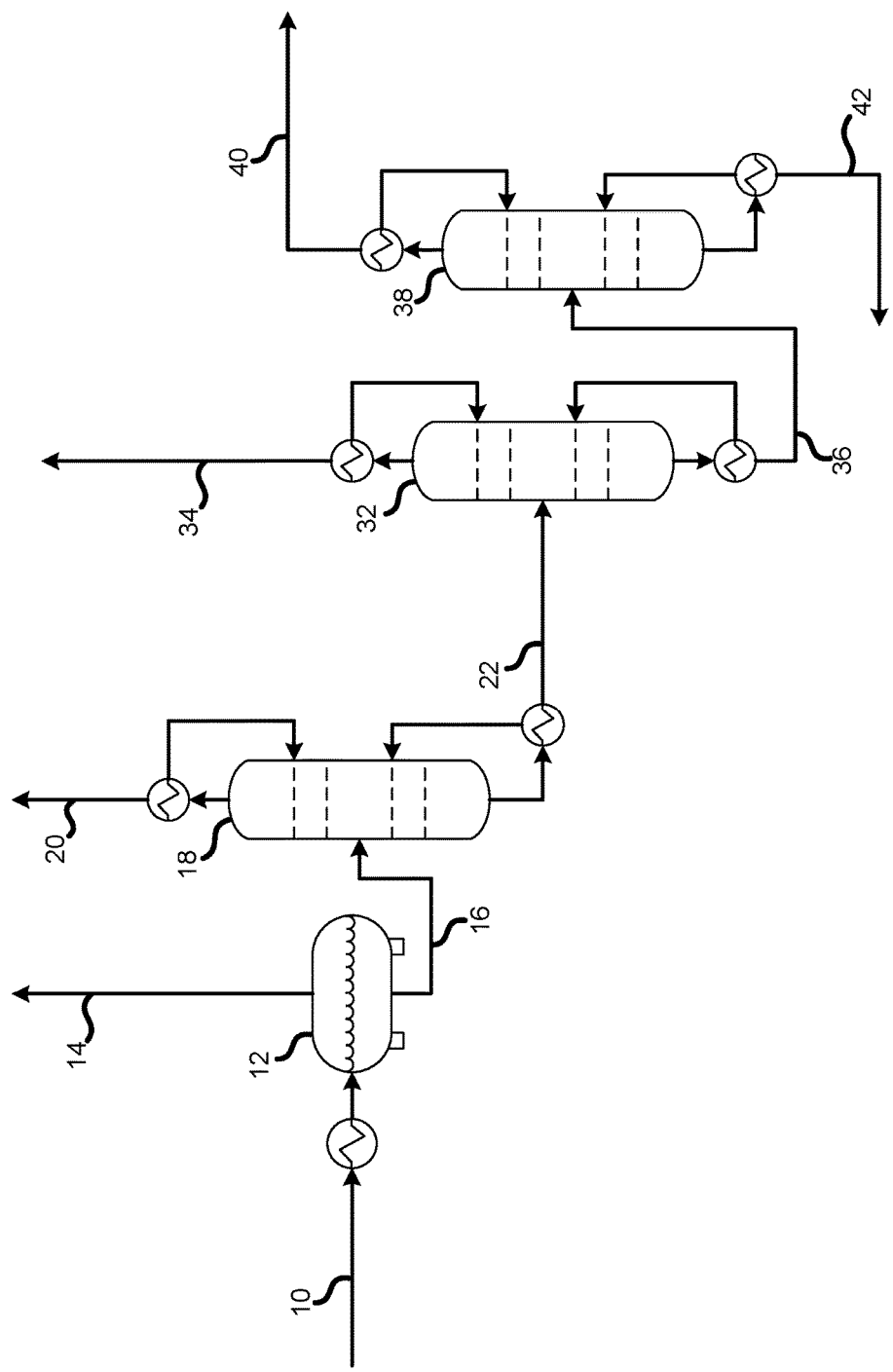
FIG. 2 is a schematic diagram of the first step of the present process according to a second embodiment.

Referring to FIG. 2, the first step of the present process is shown according to a second embodiment, wherein identical reference numerals are used to identify identical steps or components with respect to the prior embodiment described above. Referring to FIG. 2, crude HCFC-242fa is conveyed from column 18 via line 22 to a first continuous vacuum distillation column 32, and low boiling by-products are removed in overhead stream 34 and sent to collection or waste disposal. More pure HCC-242fa is removed from column 32 in bottoms stream 36 and passes to second continuous vacuum distillation column 38. More pure HCFC-242fa is removed from column 38 in overhead stream 40 and conveyed to the second step of the present process, described below. High boiling point by-products, such as HCFC-241fa, 1233zd dimers, and other halogenated compounds containing 4 or more carbon atoms, are removed from column 38 in bottom stream 42 and sent to collection or waste disposal.

Figure 3:
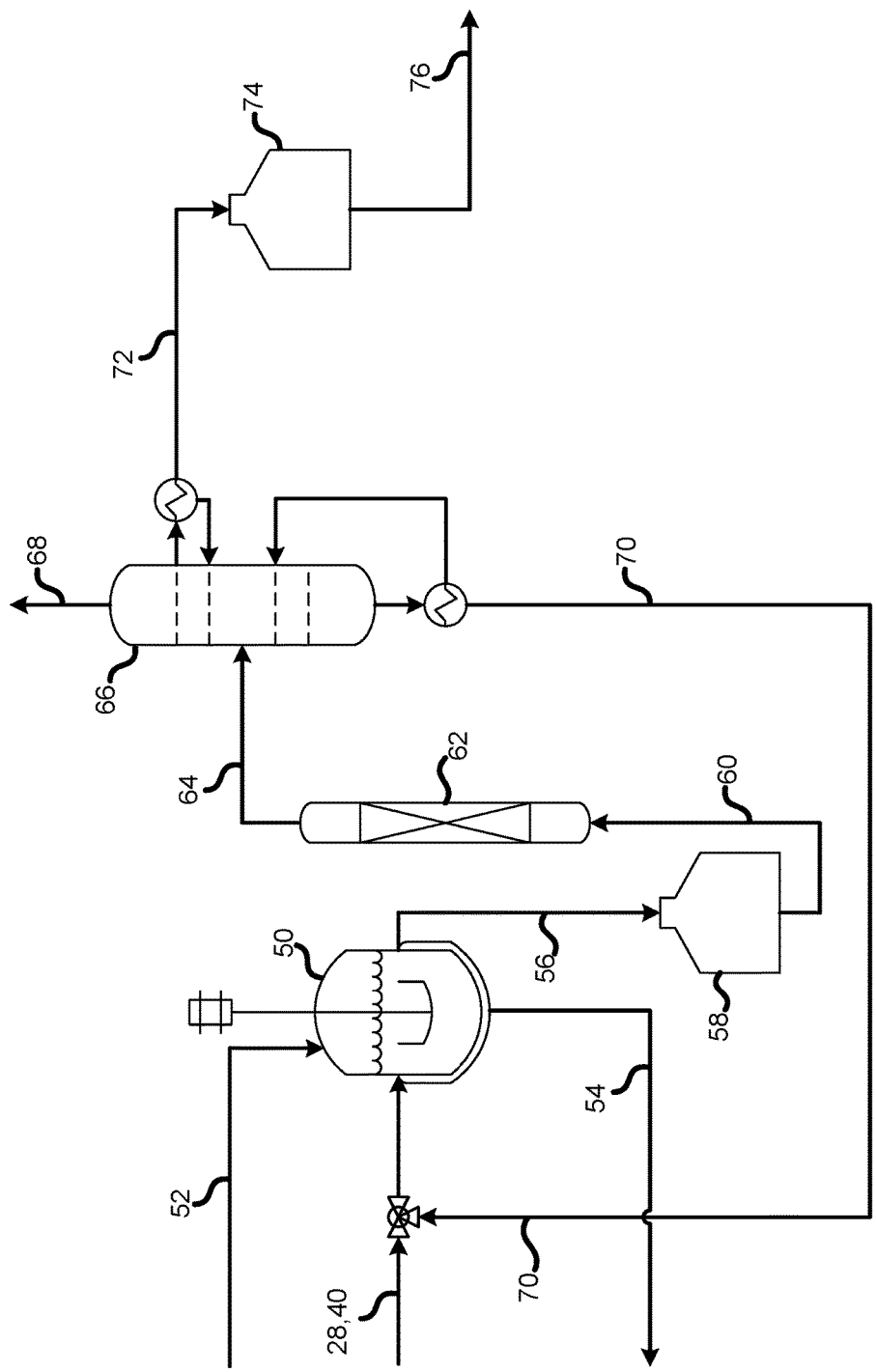
FIG. 3 is a schematic diagram of the second step of the present process according to a first embodiment.

Referring to FIG. 3, a schematic of the second step of the present process is shown according to a first embodiment. Referring to FIG. 3, HCFC-242fa from the first step is conveyed to dehydrochlorination reactor 50 via line 28, 40 (FIGS. 1 and 2). A basic solution is also conveyed to reactor 50, either via a separate line 52 or may be combined into the HCFC-242fa stream of line 28, 40. In reactor 50, the HCFC-242fa is dehydrochlorinated in the presence of a basic solution to form HCFO-1232zd. Spent basic solution is conveyed from reactor 50 via line 54 as waste. The crude HCFO-1232zd is conveyed from reactor 50 via line 56 to a storage tank 58, and thence via line 60 to drying column 62, which includes a suitable desiccant for removing moisture. Thereafter, the crude HCFO-1232zd is conveyed via line 64 to a batch vacuum distillation column 66. Low boiling by-products are removed from column 66 in overhead stream 68 and are conveyed to collection or waste disposal. High boiling by-products, such as unreacted HCFC-242fa and others, are removed from column 66 in bottoms stream 70 and recycled back to either the HCFC-242fa stream of line 28, 40 or reactor 50. Purified HCFO-1232zd is conveyed from column 66 via line 72 to storage tank 74 and then passes via line 76 to the third step of the present process, described below.

Figure 4:
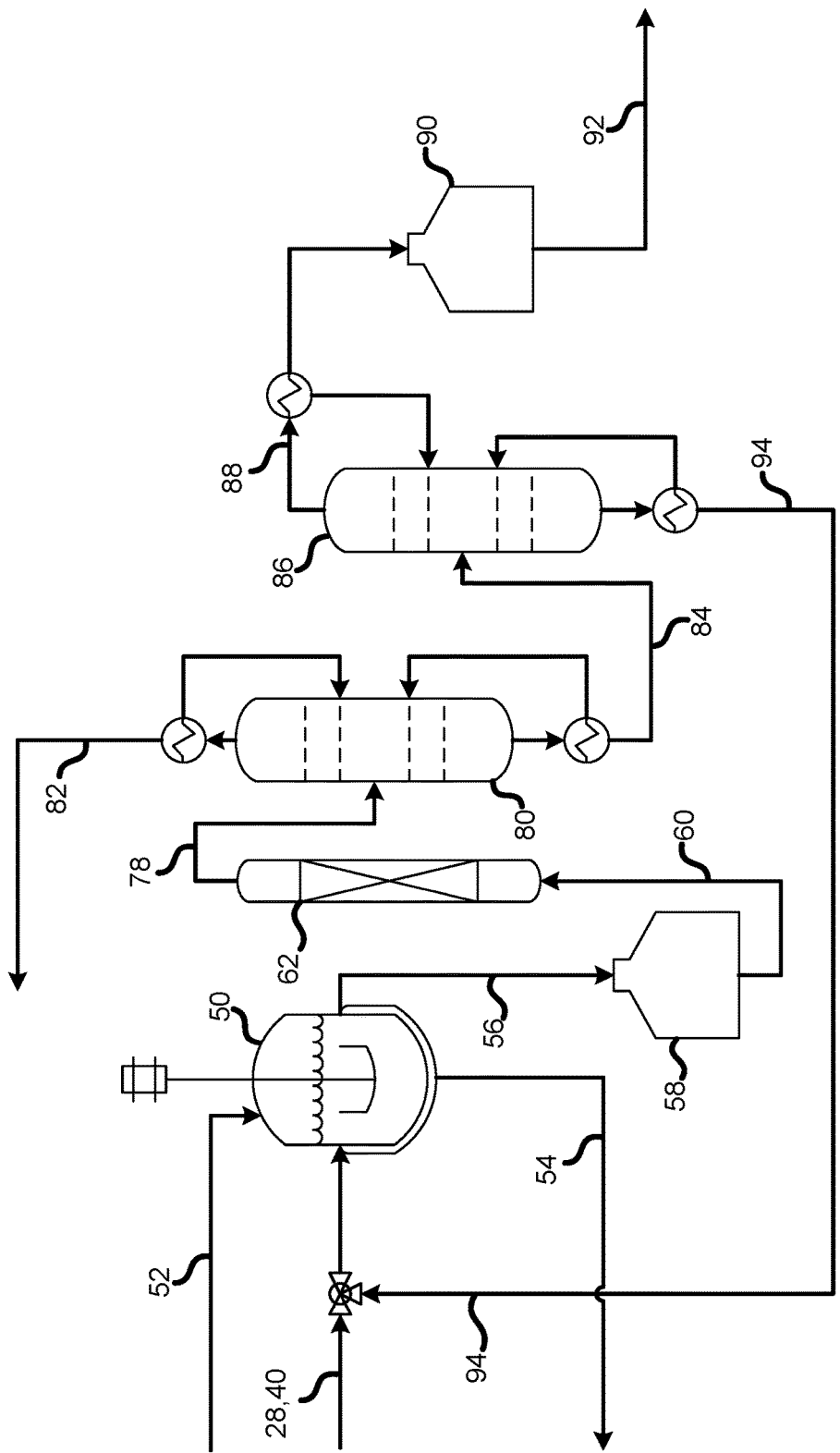
FIG. 4 is a schematic diagram of the second step of the present process according to a second embodiment.

Referring to FIG. 4, a schematic of the second step of the present process is shown according to a second embodiment, wherein identical reference numerals are used to identify identical steps of components with respect to the prior embodiment described above. Referring to FIG. 4, the dried HCFO-1232zd from drying column 62 is conveyed via line 78 to a first continuous vacuum distillation column 80. An overhead stream 82 of low boiling by-products is removed from column 80 to collection or waste disposal. More pure HCFO-1232zd is removed from column 80 as bottoms stream 84 and conveyed to a second continuous vacuum distillation column 86. Purified HCFO-1232zd is removed from column 86 in overhead stream 88 and conveyed to storage tank 90, and thence via line 92 to the third set of the present process, described below. High boiling by-products, such as unreacted HCFC-242fa and others, are removed from column 86 as bottoms stream 94 and recycled back to either HCFC-242fa input line 28, 40 or reactor 50.

Figure 5:
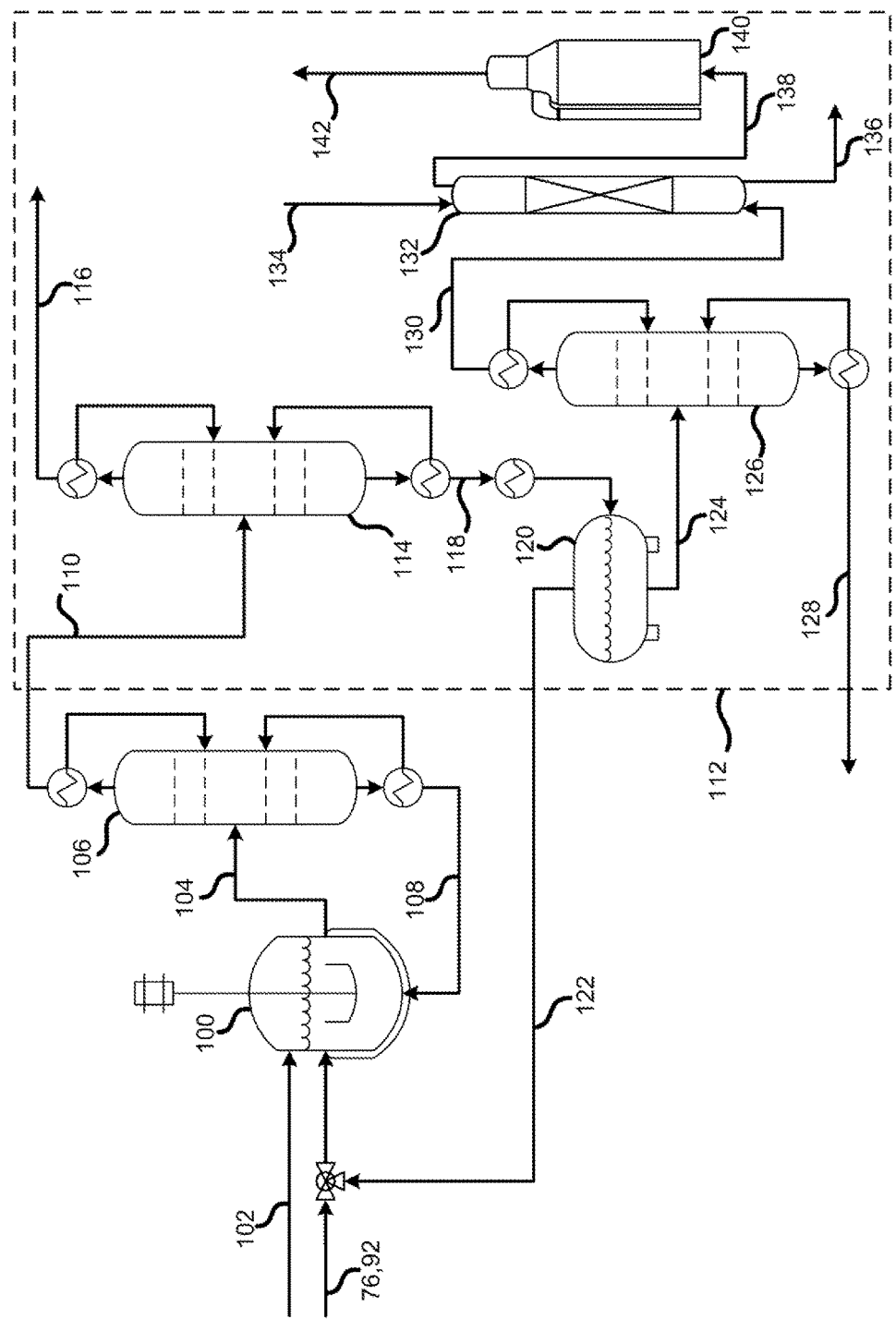
FIG. 5 is a schematic diagram of a first portion of the third step of the present process.
Figure 6:
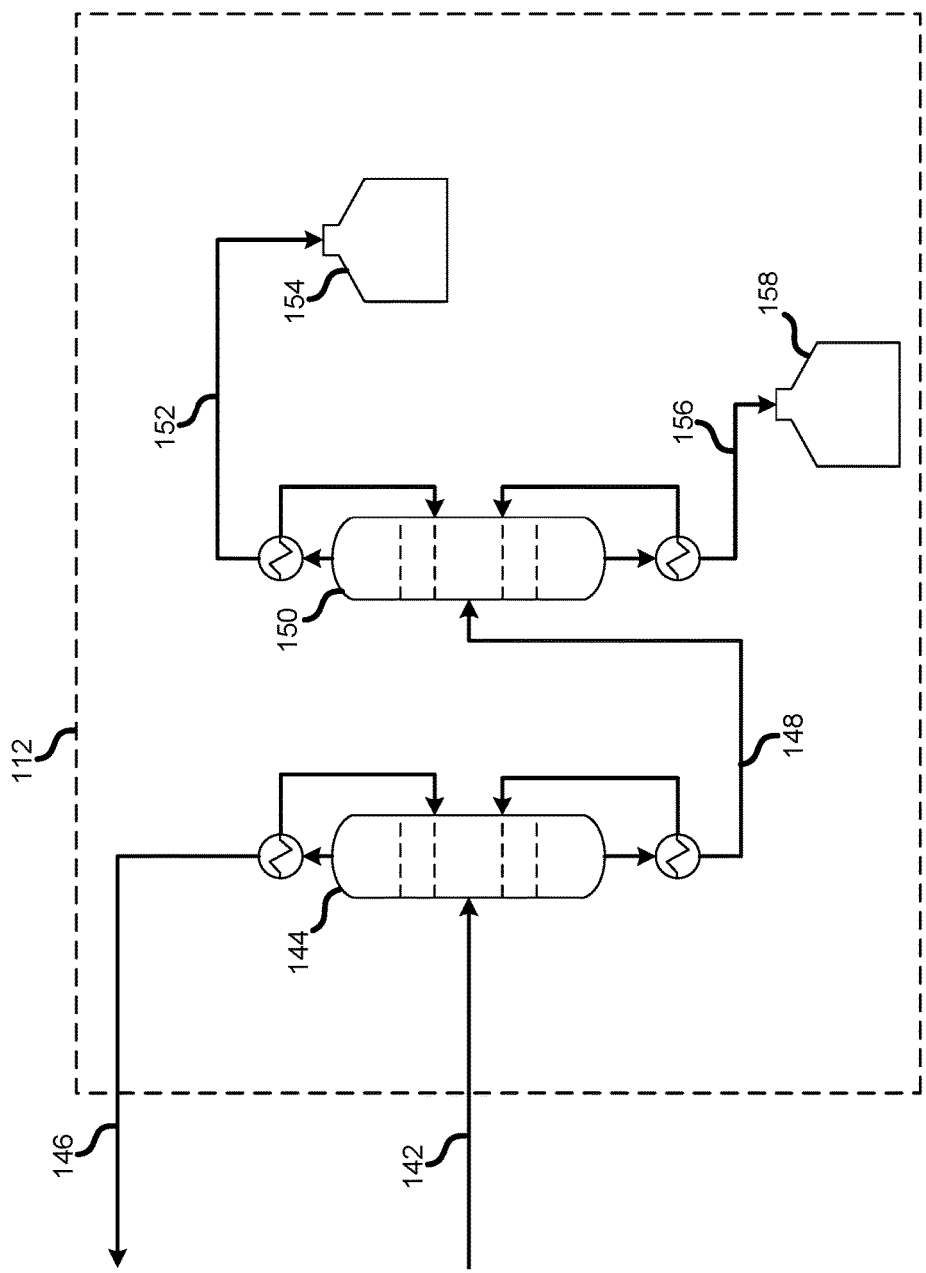
FIG. 6 is a schematic diagram of a second portion of the third step of the present process.

Referring to FIGS. 5 and 6, schematics of the third step of the present process are shown. Referring to FIG. 5, purified HCFO-1232zd from the second step of the present process is conveyed to fluorination reactor 100 via line 76, 92 (FIGS.

3 and 4) along with a supply of HF via line 102, and crude HCFO-1233zd and by-products formed in reactor 100 are conveyed from reactor 100 via line 104 to recycle distillation column 106. High boiling by-products, such as unreacted HCFO-1232zd and HF, are removed from column 106 in bottoms stream 108 and are recycled back to reactor 100. Crude HCFO-1233zd is removed from column 106 in overhead stream 110 to an HCl recovery, organic/HF recycle, and HCFO-1233zd purification stage 112.

In stage 112, a first distillation column 114 is used to separate HCl as overhead stream 116, which may be isolated as a co-product, for example. HCFO-1233zd in bottoms stream 118 is conveyed to phase separator 120, where HF and HCFO-1233zd separate via gravity, with the separated upper phase HF conveyed from phase separator 120 via recycle line 122 back to fluorination reactor 100, or merged into either line 76, 92 or HF input stream 102. The separated lower phase HCFO-1233zd is conveyed from phase separator 120 via line 124 to distillation column 126, wherein high boiling by-products are separated via bottoms stream 128 to a collection vessel or waste disposal, for example. HCFO-1233zd is removed via overhead stream 130 and conveyed to a scrubber column 132, in which water or a weak basic solution is conveyed into column 132 via inlet 134 to remove any residual HF as water or spent basic solution via outlet 136. The scrubbed HCFO-1233zd is then conveyed via line 138 to drying column 140 to remove any residual moisture using a desiccant, for example, and the dried HCFO-1233zd is then conveyed via line 142 to the further steps shown in FIG. 10.

Referring to FIG. 6, dried HCFO-1233zd is conveyed to lights distillation column 144 via line 142, where low boiling by-products are separated in overhead stream 146 and may be collected in a collection vessel or waste disposal. HCFO-1233zd(E) is removed from column 144 in bottoms stream 148 and conveyed to product distillation column 150, where the purified HCFO-1233zd(E) is removed from column 150 in overhead stream 152 and collected within collection container 154. High boiling co-products, such as HCFO-1233zd(Z), which is typically a majority by-product, HCFC-244fa as a next most abundant by-product, a minor amount of HCFC-243fa, and very small amounts of other by-products, are removed from column 150 in bottoms stream 156 and are collected within collection container 158.

EXAMPLES

Example 1

Exemplary Isolated HCFC-242fa Compositions

Relatively pure HCFC-242fa was isolated from a HCFO-1233zd crude product stream that was produced by the continuous non-catalytic reaction of HCC-240fa and HF at temperatures between 266-284 OF (130-140° C.) and pressures between 2.41-2.75 Mpa. Table 1 below shows the composition of the HCFO-1233zd crude stream produced in the reaction after a recycle column, HCl removal column, and HF/1233zd phase separator, which returns a bottoms stream containing the majority of the unreacted anhydrous HF and HCC-240fa, and intermediates HCFO-1231zd, HCFO-1232zd, and HCFC-241fa back to the reactor for further conversion.

TABLE 1

Average composition of a sample of a HCFO-1233zd crude stream collected from a continuous non-catalytic process after a recycle column, HCl removal column, and HF/1233zd phase separator

| Component | wt % |
|---|---|
| HF | 1.9 |
| HFC-245fa | 0.14 |
| HFO-1234ze isomer 1 | 0.69 |
| HFO-1234ze isomer 2 | 0.20 |
| HCFC-244fa | 0.74 |
| HCFO-1233zd isomers | 79.46 |
| HCFC-243 isomers | 2.06 |
| HCFC-242fa | 13.44 |
| HCFC-242fb | 0.32 |
| HCFC-241 isomer | 0.73 |
| HCFO-1232 isomers | 0.04 |
| others | 0.29 |

Table 2 below shows the composition of an HCFC-242fa crude stream produced after the HCFO-1233zd crude stream is continuously distilled to remove low boiling components.

TABLE 2

Composition of a high boiler stream after continuous distillation of a HCFO-1233zd crude stream from Table 1 to remove HF and the majority of compounds with nBP ≤ 25° C.

| Component | GC area % |
|---|---|
| HCFC244fa | 1.61 |
| HCFO1233zd isomers | 3.14 |
| HCFC243 isomers | 8.85 |
| HCFC242fa | 82.64 |
| HCFC242fb | 1.62 |
| HCFC241 isomer | 1.62 |
| HCFO1232 isomers | 0.08 |
| others | 0.44 |

*About 1-2 ppm HF present per ion chromatography (IC) analysis

Table 3 below shows a 99.86 GC area % pure HCFC-242fa stream produced from the vacuum batch distillation of the HCFC-242fa crude stream produced as described in Table 2 above.

TABLE 3

Composition of stream after vacuum batch distillation of the high-boiler stream from Table 2 to purify 242fa

| Component | GC area % |
|---|---|
| HCFC243 isomers | 0.14 |
| HCFC242fa | 99.86 |

*<1 ppm HF present per ion chromatography (IC) analysis

Example 2

Separation of HCFC-242fa and HF 12.2 grams of the greater than 99.8 GC area % purity HCFC-242fa produced in Example 1 was added to 13.2 grams of anhydrous HF in a perfluoroalkoxy (PFA) sample container. The container was mixed by shaking, and was then placed in wet ice and allowed to settle and cool to about 0° C. The HF and organic were not miscible as two distinct phases were present. The bottom HCFC-242fa phase was sampled and analyzed by ion chromatography (IC) to measure HF content, and was found to contain 1.3 wt. % HF.

Example 3

Conversion of HCFC-242fa to HCFO-1232zd 1200 grams of HCFC-242fa with a purity of 99.84% produced in Example 1 was added to a 3 L round bottom flask equipped with a glass mixer. 1 liter of 7.5% KOH solution was added to the HCFC-242fa and the mixer was turned on at ambient temperature (20-21° C.). The progress of the reaction was monitored by taking a sample of the organic liquid and analyzing with a gas chromatograph (GC). The spent KOH solution was decanted and replaced with fresh 7.5% KOH solution every 16 hours for 48 hours. The organic phase was recovered using a separatory funnel, washed with water to remove any salts that may have dissolved in the organic and then dried with calcium sulfate. 1029 grams of organic was recovered giving a 97.0% mass balance. The resulting washed and dried organic was analyzed by gas chromatography (GC). The conversion of HCFC-242fa was 97.1% and the selectivity to HCFO-1232zd was 90.7 mole % and balance (9.3%) others.

Example 4

Separation of HCFO-1232zd

In this Example, 268 grams of 99.8+GC area % HCFO-1232zd was isolated from the vacuum distillation of the HCFO-1232zd crude which was produced in Example 3.

Example 5

Production of HCFO-1233zd

In this Example, the uncatalyzed chemical reaction for forming HCFO-1233zd(E) was further studied. In particular, the theory that starting with an unsaturated hydrochlorofluoroolefin (HCFO) such as HCFO-1232zd, as opposed to the saturated HCC-240fa or HCFC-242fa would be more selective to 1233zd(E) via a much faster reaction (higher conversion for a given set of operating conditions) was tested. Several batch reaction experiments individually starting with the foregoing organic feed stocks were tested for the purpose of comparing conversion and selectivity to HCFO-1233zd(E) using an identical series of operating conditions for each of the feed stocks.

Reactions for all three feed stocks were run at 140° C. with a 1 hour hold time and 130° C. with a 3 hour hold time. Batch reaction experiments using HCFC-242fa and HCFO-1232zd only, were run at 130° C. with a 1 hour hold time. All experiments used similar HF to organic mole ratios of about 17:1. These results are shown in FIGS. 7-9 and summarized below.

At all operating conditions the conversion of HCFO-1232zd was equal to or greater than 99.8% and the selectivity to HCFO-1233zd(E) was between 89.5 and 94.3%. The conversion of HCC-240fa was about 99.5%, but the selectivity to HCFO-1233zd(E) ranged from only 66.3 to 77.0 (respectively for the 140° C. and 130° C. experiments). The conversion of HCFC-242fa were 4.4%, 3.9%, and 1.6%, respectively, for the three experiments and the selectivity to HCFO-1233zd(E) was only 18.2%, 28.3%, and 32.4% for the three experiments.

These results indicate that starting with HCFO-1232zd feedstock to produce HFCO-1233zd(E) via a non-catalytic liquid phase reaction is superior in terms of conversion and/or HCFO-1233zd(E) selectivity in comparison with the use of HCC-240fa or HCFC-242fa feedstocks.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

While this disclosure has been described as relative to exemplary designs, the present disclosure may be further modified within the spirit and scope of this disclosure. Further, this application is intended to cover such departures from the present disclosure as come within known or customary practice in the art to which this disclosure pertains.

The invention claimed is:
1. A process for the production of 1-chloro-3,3,3-trifluoropropene (HCFO-1233zd), comprising the steps of:
 providing a reactant composition including 1,3,3-trichloro-1,1-difluoropropane (HCFC-242fa);
 dehydrochlorinating the HCFC-242fa in the presence of a basic solution to form 1,3-dichloro-3,3-difluoropropene (HCFO-1232zd); and
 fluorinating the HCFO-1232zd with hydrogen fluoride (HF) to produce HCFO-1233zd.
2. The process of claim 1 wherein following said fluorinating step, the HCFO-1233zd produced is predominantly HCFO-1233zd(E).
3. The process of claim 1, wherein said dehydrochlorinating step is performed at a temperature between 0° C. and 100° C.
4. The process of claim 1, wherein said fluorinating step is performed at a temperature between 80° C. and 150° C.
5. The process of claim 1, wherein said fluorinating step is performed in the absence of a catalyst.
6. The process of claim 1, wherein the reactant composition further includes hydrogen fluoride (HF) and said process further includes the additional step, after said providing step and prior to said dehydrochlorinating step, of separating HF from the reactant composition.
7. The process of claim 1, further comprising the additional step, after said dehydrochlorinating step and prior to said fluorinating step, of drying the HCFO-1232zd.
8. The process of claim 1, wherein the basic solution in said dehydrochlorinating step is selected from the group consisting of potassium hydroxide (KOH), sodium hydroxide (NaOH), and calcium hydroxide (CaOH).
9. A process for the production of 1-chloro-3,3,3-trifluoropropene (HCFO-1233zd), comprising the steps of:
 fluorinating 1,1,1,3,3-pentachloropropane (HCC-240fa) with hydrofluoric acid (HF) to produce a product stream including HCFO-1233zd and 1,3,3-trichloro-1,1-difluoropropane (HCFC-242fa);
 separating HCFC-242fa from the product stream;
 dehydrochlorinating the HCFC-242fa in a liquid phase in the presence of a basic solution to form 1,3-dichloro-3,3-difluoropropene (HCFO-1232zd); and
 fluorinating the HCFO-1232zd with hydrogen fluoride (HF) to produce HCFO-1233zd.

10. The process of claim 9, wherein said first fluorinating step is performed at a reaction temperature between 120° C. and 140° C. and at a reaction pressure of between 230 psig and 400 psig.

11. The process of claim 9 wherein, following said second fluorinating step, the HCFO-1233zd produced is predominantly HCFO-1233zd(E).

12. The process of claim 9, wherein said dehydrochlorinating step is performed at a temperature between 0° C. and 100° C.

13. The process of claim 9, wherein said second fluorinating step is performed at a temperature between 80° C. and 150° C.

14. The process of claim 9, wherein said second fluorinating step is performed in the absence of a catalyst.

15. The process of claim 9, wherein said process further includes an additional step, after said first fluorinating step and prior to said separating step, of separating HF from the product stream.

16. The process of claim 9, further comprising the additional step, after said dehydrochlorinating step and prior to said second fluorinating step, of drying the HCFO-1232zd.

17. The process of claim 9, further comprising the additional step, after said second fluorinating step, of recycling at least one of unreacted HCFO-1232zd and unreacted HF back to said first fluorinating step.

18. The process of claim 9, wherein said separating step is conducted via vacuum distillation.

19. The process of claim 9, wherein said separating step is conducted via distillation at a pressure between 10 torr and 5,200 torr.

* * * * *